(12) United States Patent
Shi et al.

(10) Patent No.: US 7,635,853 B1
(45) Date of Patent: Dec. 22, 2009

(54) ANALYZING REFLECTION DATA FOR RECORDING MEDIUM IDENTIFICATION

(75) Inventors: Yang Shi, San Diego, CA (US); Gregory Michael Burke, San Diego, CA (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 12/250,717

(22) Filed: Oct. 14, 2008

(51) Int. Cl.
*G01N 21/86* (2006.01)
*B41J 2/01* (2006.01)

(52) U.S. Cl. ............................ 250/559.04; 250/559.01; 347/14; 347/101

(58) Field of Classification Search ............ 250/559.01, 250/559.04, 559.06, 559.07, 221; 347/14, 347/16, 101, 105; 356/446, 600
See application file for complete search history.

(56) References Cited

U.S. PATENT DOCUMENTS

| | | | |
|---|---|---|---|
| 5,764,251 A | 6/1998 | Hashimoto | 347/16 |
| 6,291,829 B1 | 9/2001 | Allen et al. | 250/559.07 |
| 6,325,505 B1 | 12/2001 | Walker | 347/105 |
| 6,386,669 B1 | 5/2002 | Scofield et al. | 347/14 |
| 6,561,643 B1 | 5/2003 | Walker et al. | 347/105 |
| 6,838,687 B2 | 1/2005 | Tullis et al. | 250/559.07 |
| 6,914,684 B1 | 7/2005 | Bolash et al. | 356/600 |
| 6,984,034 B2 | 1/2006 | Tsujimoto | 347/105 |
| 2007/0194257 A1* | 8/2007 | Cheong et al. | 250/559.4 |

* cited by examiner

*Primary Examiner*—Kevin Pyo
(74) *Attorney, Agent, or Firm*—Stephen H. Shaw

(57) ABSTRACT

A method is proved for analyzing frequency distribution of a reflection from a surface of a body to determine a type of body surface. Initially, a plurality of data points from a sensor that senses the reflection of the body's surface are provided. A first series of terms are summed together to provide a first magnitude, each term including a plurality of data points; wherein the plurality of data points being spaced apart by a first spacing. A second series of terms are summed together to provide a second magnitude, each term including a plurality of data points; wherein the plurality of data points being spaced apart by a second spacing. The first magnitude is compared to the second magnitude to determine the type of body surface.

20 Claims, 12 Drawing Sheets

ANALYZING REFLECTION DATA FOR RECORDING MEDIUM IDENTIFICATION

FIELD OF THE INVENTION

This invention relates generally to the field of printers, and in particular to processing of digital data corresponding to optical reflections from the surface of a recording medium, in order to identify the type of recording medium.

BACKGROUND OF THE INVENTION

In many types of printers, a printhead (for example, an inkjet printhead), including an array of marking elements, is controlled to make marks of particular sizes, colors, etc. in particular locations on recording media (sometimes generically called paper herein and used interchangeably with the term "media") in order to print a desired image. In some types of printing systems (sometimes termed "page-width printers") the array of marking elements extends across the width of the recording medium and the image can be printed one line at a time as the recording medium moves relative to the printhead. In other types of printing systems (sometimes termed "carriage printers") the printhead or printheads are mounted on a carriage that is moved past the recording medium in a carriage scan direction as the marking elements are actuated to make a swath of dots. At the end of the swath, the carriage is stopped, printing is temporarily halted, and the recording medium is advanced. Then another swath is printed, so that the image is formed swath by swath.

In order to produce high quality images, it is helpful to provide information to the printer controller electronics regarding the type of the recording medium, such as whether it is a photo paper or plain paper, for example. For inkjet printing, knowing the type of recording medium before electronically preparing the image for printing is advantageous, because differences in ink-recording medium interactions on different recording medium can result in poor image quality, if the amount and timing of ink deposition is not controlled appropriately for the type of recording medium in the printer.

Using an optical sensor to detect the type of recording medium in a printer is known in the prior art. Some examples are disclosed in U.S. Pat. Nos. 5,764,251; 6,291,829; 6,325,505; 6,386,669; 6,561,643; 6,838,687; 6,914,684; 6,984,034; and co-pending U.S. patent application Ser. No. 12/037,970. Such an optical sensor assembly for recording medium type detection can optionally be attached to the printhead carriage of a carriage printer. In the same way that the printhead can mark on all regions of the paper by the back and forth motion of the carriage and by the advancing of the recording medium between passes of the carriage, a carriage-mounted optical sensor is able to provide optical measurements, typically of optical reflectance, for one or more regions of the paper. Other types of optical sensors include stationarily-mounted sensors that are positioned near the paper-advance path of the printer, so that one or more regions of the paper can be viewed by the sensor as the paper moves past it.

An optical sensor assembly for recording medium type detection typically includes one or more photosensors and one or more light sources, such as LED's, mounted such that the emitted light is reflected off the surface of the recording medium, and the reflected light is received in the one or more photosensors. LED's and photosensors can be oriented relative to each other such that the photosensor receives specular reflections of light emitted from an LED (i.e., light reflected from the recording medium at the same angle as the incident angle relative to the normal to the nominal plane of the recording medium) or diffuse reflections of light emitted from an LED (i.e., light reflected from the recording medium at a different angle than the angle of incidence).

Typically, the photosensor signals for specular and/or diffuse reflections of light from the surface of the recording medium are amplified and then processed to separate the signal from the background noise. The processed signal characteristics are then compared with known signal characteristics for different recording medium types, and the present recording medium type is identified.

One known way in which recording medium types can be distinguished from one another is the spatial frequency of the variation of optical reflectance from the surface of the recording medium. It is known, for example, that photo papers made for inkjet printing tend to have a specular optical reflectance that has a spatial frequency of variation that is dominated by high frequency components, and that plain papers tend to have a specular optical reflectance that has a spatial frequency of variation that is dominated by comparatively lower frequency components.

Automatic detection of recording medium type in a printer is desired to be: a) highly accurate, so that the correct recording medium type is dependably identified; b) fast, so that printing throughput is not adversely impacted due to waiting for identification of the recording medium type; c) robust, so that aging or contamination of the light source or photosensor, or different environmental conditions do not degrade the reliability of recording medium type identification; and d) simple so that it can be done with low cost.

Different trade-offs in recording medium type identification requirements can be made in different types of printing systems. For example, U.S. Pat. Nos. 6,325,505 and 6,561,643, disclose performing a Fourier transform on the reflectance data to quantify the spatial frequency components. This may be appropriate for printers that are always connected to a host computer, because Fourier transform analysis can require extensive processing in order to be done quickly. However, all-in-one printing systems that include a scanner as well as a printer; are sometimes operated in a standalone mode for copying photos and documents, and it is important that the recording medium type identification still be fast, accurate, reliable, and simple. In low-cost all-in-one printing systems the system controller may be a "system-on-a-chip" controller, which is inexpensive, but may not have the processing bandwidth for complex calculations for recording medium type identification.

Some types of simple and fast signal processing methods for photosensor reflectance data for recording medium type identification are found to be highly accurate when the printing system is new, but as the sensor assembly ages or the optical components become coated with ink mist or particulates, or encounter extreme environmental conditions, the resulting shift in the processed signal characteristics can cause occasional misidentification with a set of known signal characteristics so that accuracy of recording medium type identification is not as high as it was initially. As a result, occasional recalibration may be required in order to restore the accuracy. While such recalibration can be automatic and programmed into printer firmware for implementation, it is preferable in some embodiments to provide a signal processing method that is more robust in its accuracy of recording medium type identification.

Therefore, what is needed is a new method of signal processing that is simple, fast, robust, and effective in analyzing a frequency distribution for accurate identification of a type of recording medium or other body types by reflections from their surfaces.

SUMMARY OF THE INVENTION

A method is proved for analyzing frequency distribution of a reflection from a surface of a body to determine a type of body surface. Initially, a plurality of data points from a sensor that sense the reflection of the body's surface are provided. A first series of terms are summed together to provide a first magnitude, each term including a plurality of data points; wherein the plurality of data points being spaced apart by a first spacing. A second series of terms are summed together to provide a second magnitude, each term including a plurality of data points; wherein the plurality of data points being spaced apart by a second spacing. The first magnitude is compared to the second magnitude to determine the type of body surface.

DETAILED DESCRIPTION OF THE INVENTION

Figure 1:
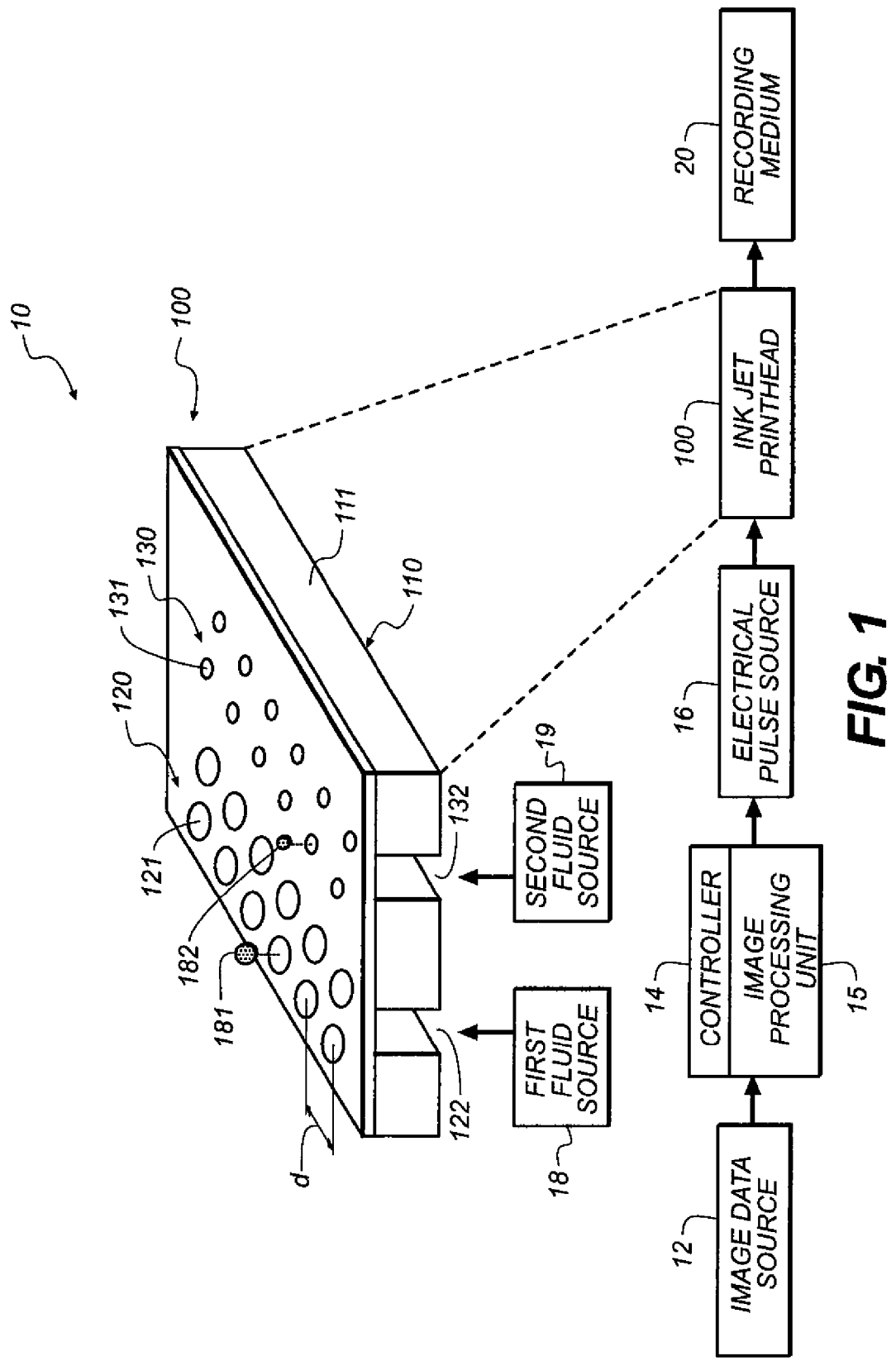
FIG. 1 is a schematic representation of an inkjet printer system.

Referring to FIG. 1, a schematic exemplary representation of an inkjet printer system 10 that incorporates the present invention described further herein is shown. Printer system 10 includes a source 12 of image data, which provides data signals that are interpreted by a controller 14 as being commands to eject drops. Controller 14 includes an image processing unit 15 for rendering images for printing, and outputs signals to a source 16 of electrical energy pulses that are inputted to an inkjet printhead 100, which includes at least one printhead die 110.

In the example shown in FIG. 1, there are two nozzle arrays. Nozzles 121 in the first nozzle array 120 have a larger opening area than nozzles 131 in the second nozzle array 130. In this example, each of the two nozzle arrays has two staggered rows of nozzles, each row having a nozzle density of 600 per inch. The effective nozzle density then in each array is 1200 per inch. If pixels on the recording medium were sequentially numbered along the paper advance direction, the nozzles from one row of an array would print the odd numbered pixels, while the nozzles from the other row of the array would print the even numbered pixels.

In fluid communication with each nozzle array is a corresponding ink delivery pathway. Ink delivery pathway 122 is in fluid communication with nozzle array 120, and ink delivery pathway 132 is in fluid communication with nozzle array 130. Portions of fluid delivery pathways 122 and 132 are shown in FIG. 1 as openings through printhead die substrate 111. One or more printhead die 110 will be included in inkjet printhead 100, but only one printhead die 110 is shown in FIG. 1. The printhead die are arranged on a support member as discussed below relative to FIG. 2. In FIG. 1, first ink source 18 supplies ink to first nozzle array 120 via ink delivery pathway 122, and second ink source 19 supplies ink to second nozzle array 130 via ink delivery pathway 132. Although distinct ink sources 18 and 19 are shown, in some applications it may be beneficial to have a single ink source supplying ink to nozzle arrays 120 and 130 via ink delivery pathways 122 and 132 respectively. Also, in some embodiments, fewer than two or more than two nozzle arrays can be included on printhead die 110. In some embodiments, all nozzles on a printhead die 110 can be the same size, rather than having multiple sized nozzles on a printhead die.

Not shown in FIG. 1, are the drop forming mechanisms associated with the nozzles. Drop forming mechanisms can be of a variety of types, some of which include: a heating element to vaporize a portion of ink and thereby cause ejection of a droplet; a piezoelectric transducer to constrict the volume of a fluid chamber and thereby cause ejection; or an actuator which is made to move, for example, by heating a bilayer element, and thereby cause ejection. In any case, electrical pulses from pulse source 16 are sent to the various drop ejectors according to the desired deposition pattern. In the example of FIG. 1, droplets 181 ejected from nozzle array 120 are larger than droplets 182 ejected from nozzle array 130, due to the larger nozzle opening area. Typically other aspects of the drop forming mechanisms (not shown) associated respectively with nozzle arrays 120 and 130 are also sized differently in order to optimize the drop ejection process for the different sized drops. During operation, droplets of ink are deposited on a recording medium 20.

Figure 2:
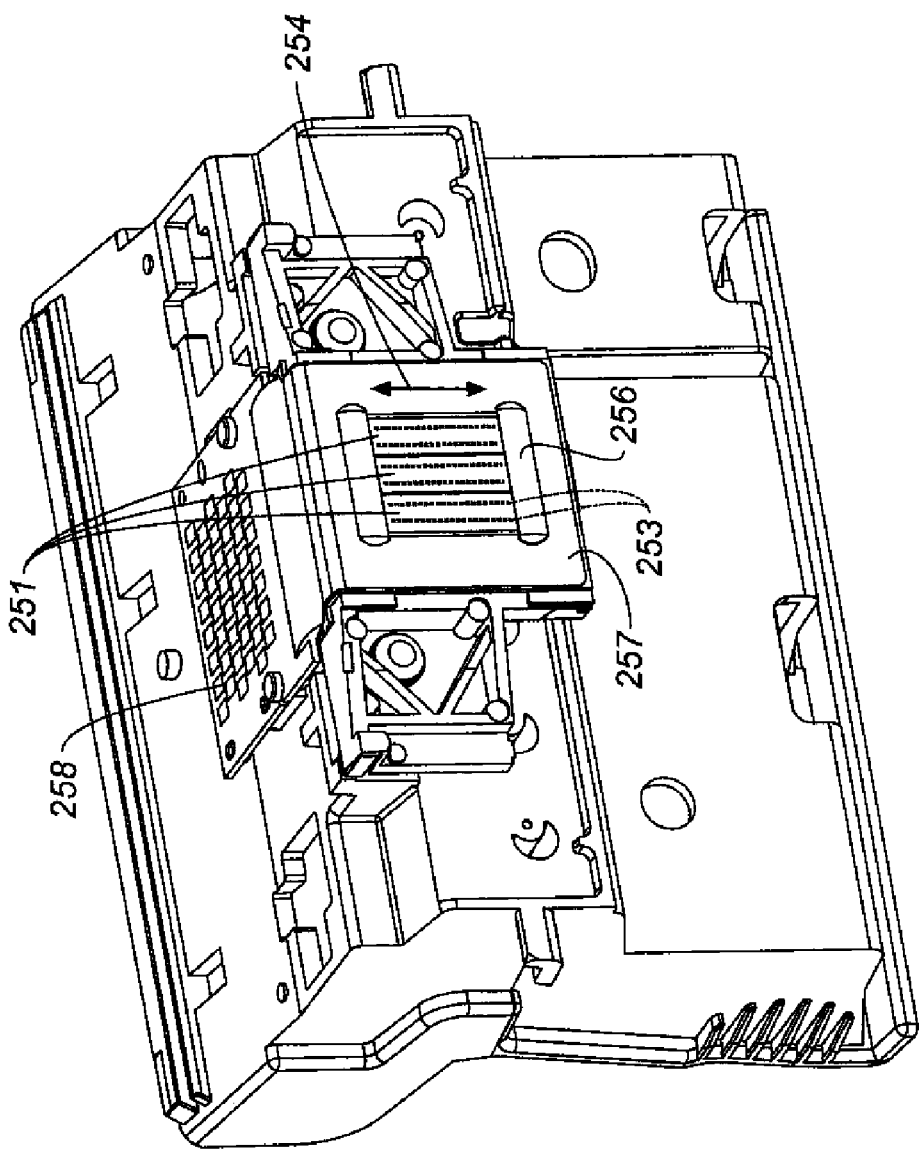
FIG. 2 is a perspective view of a portion of a printhead chassis.

FIG. 2 shows a perspective view of a portion of a printhead chassis 250, which is an example of an inkjet printhead 100. Printhead chassis 250 includes three printhead die 251 (similar to printhead die 110), each printhead die containing two nozzle arrays 253, so that printhead chassis 250 contains six nozzle arrays 253 altogether. The six nozzle arrays 253 in this example may be each connected to separate ink sources (not shown in FIG. 2), such as: cyan, magenta, yellow, text black, photo black, and a colorless protective printing fluid. Each of the six nozzle arrays 253 is disposed along direction 254, and the length of each nozzle array along direction 254 is typically on the order of 1 inch or less. Typical lengths of recording medium are 6 inches for photographic prints (4 inches by 6 inches) or 11 inches for 8.5 inch by 11 inch paper. Thus, in order to print the full image, a number of swaths are successively printed while moving printhead chassis 250 across the recording medium. Following the printing of a swath, the recording medium is advanced along a recording medium advance direction 304 that is substantially parallel to nozzle array direction 254.

Also shown in FIG. 2 is a flex circuit 257 to which the printhead die 251 are electrically interconnected, for example by wire bonding or TAB bonding. The interconnections are covered by an encapsulant 256 to protect them. Flex circuit 257 bends around the side of printhead chassis 250 and connects to connector board 258. When printhead chassis 250 is mounted into the carriage 200 (see FIG. 3), connector board 258 is electrically connected to a connector (not shown) on the carriage 200, so that electrical signals may be transmitted to the printhead die 251.

Figure 3:
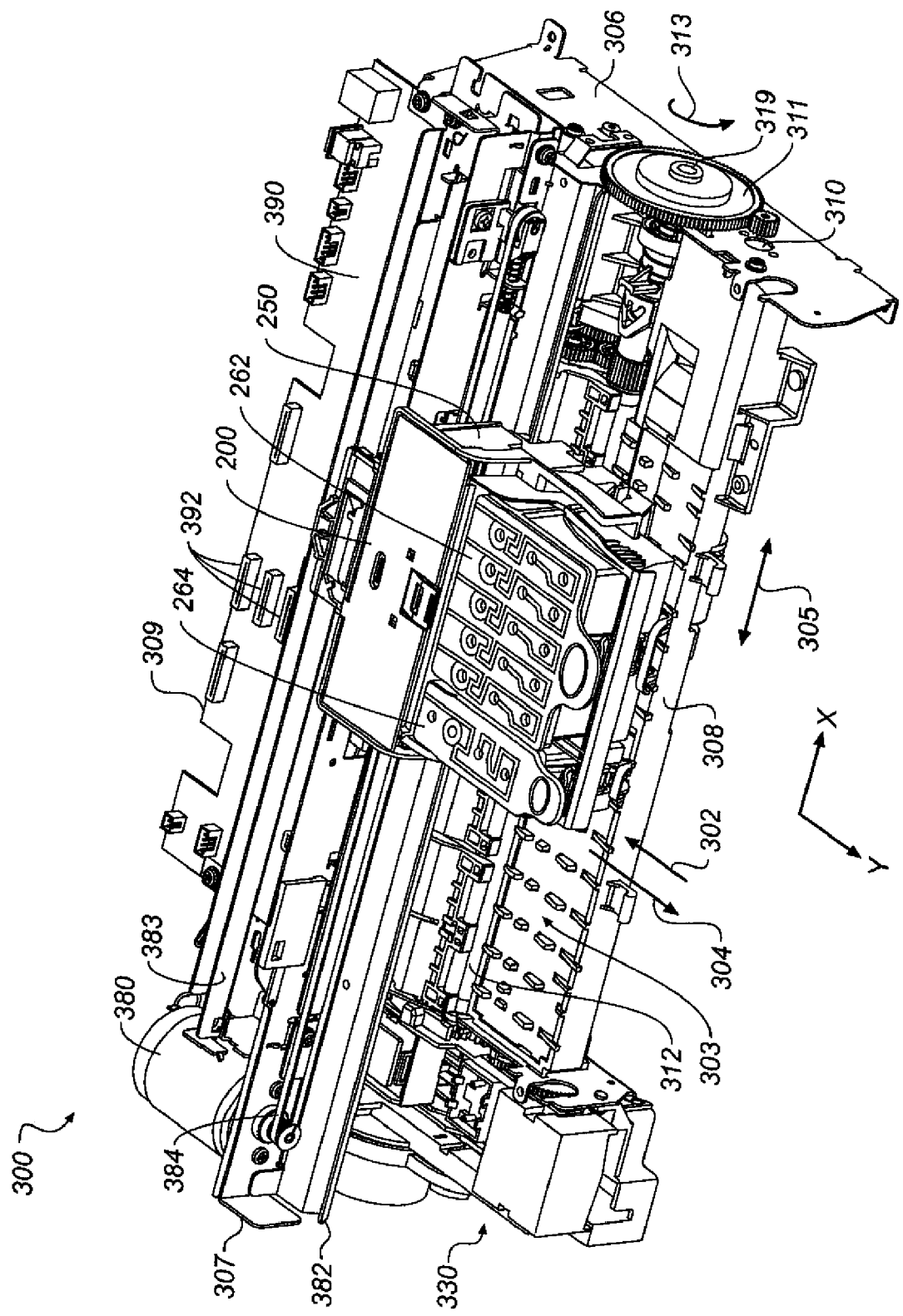
FIG. 3 is a perspective view of a portion of a carriage printer.

FIG. 3 shows a portion of a desktop carriage printer. Some of the parts of the printer have been hidden in the view shown in FIG. 3, so that other parts may be more clearly seen. Printer chassis 300 has a print region 303 across which carriage 200 is moved back and forth in carriage scan direction 305 along the X-axis, between the right side 306 and the left side 307 of printer chassis 300, while drops are ejected from printhead die 251 on printhead chassis 250 that is mounted on carriage 250. Carriage motor 380 moves belt 384 to move carriage 200 along carriage guide rail 382. An encoder sensor (not shown) is mounted on carriage 200 and indicates carriage location relative to an encoder fence 383.

Figure 4:
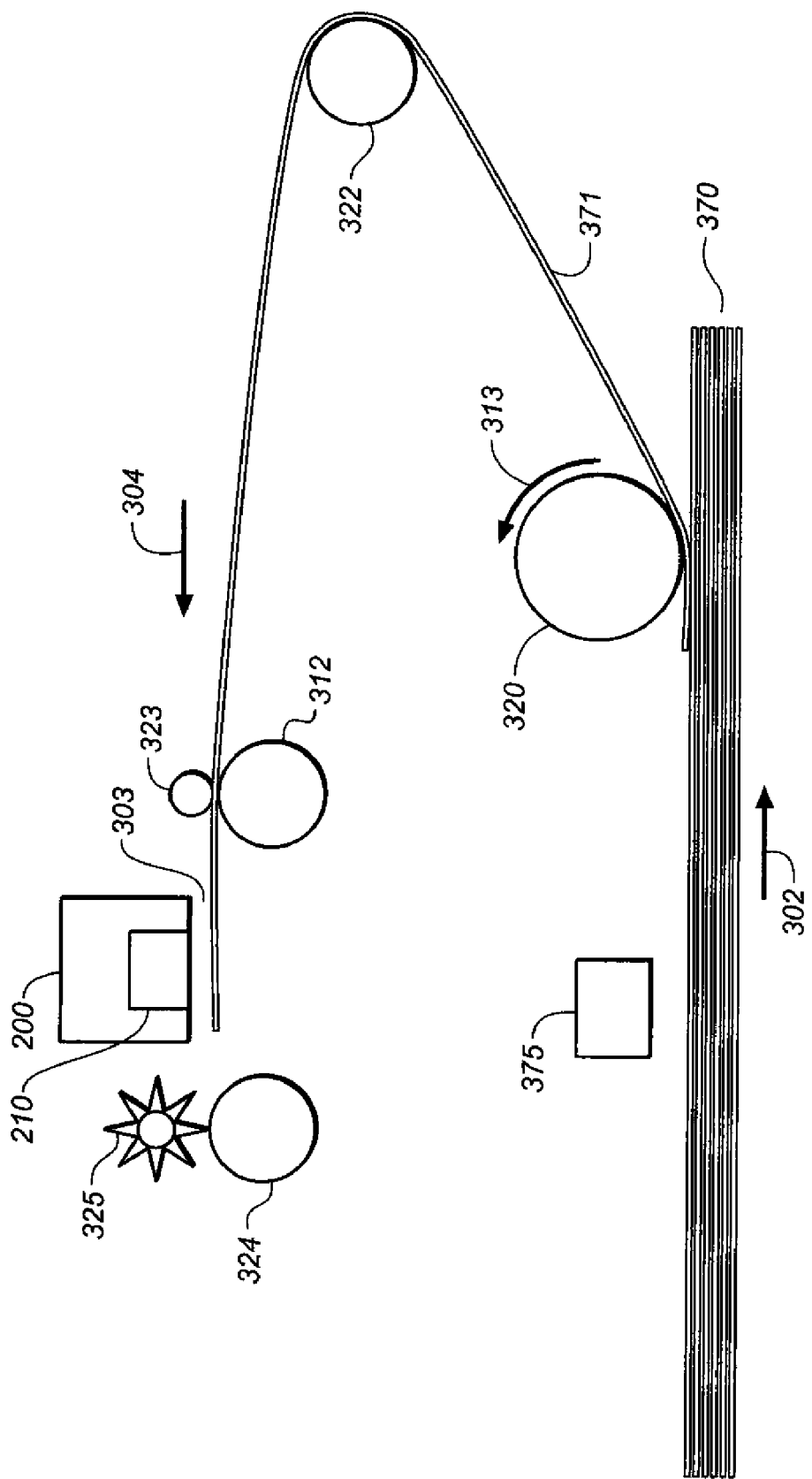
FIG. 4 is a schematic side view of a paper path in a carriage printer.

Also mounted on carriage 200 is an optical sensor (also called a carriage sensor) 210, as shown schematically in FIG. 4. Carriage sensor 210 includes a light emitter such as an LED that shines light onto the recording medium. Light reflected from the recording medium is received by a photosensor that is also included in carriage sensor 210.

Printhead chassis 250 is mounted in carriage 200, and ink supplies 262 and 264 are mounted in the printhead chassis 250. The mounting orientation of printhead chassis 250 is rotated relative to the view in FIG. 2, so that the printhead die 251 are located at the bottom side of printhead chassis 250, the droplets of ink being ejected downward onto the recording medium in print region 303 in the view of FIG. 3. Ink supply 262, in this example, contains five ink sources: cyan, magenta, yellow, photo black, and colorless protective fluid; while ink supply 264 contains the ink source for text black. Paper, or other recording medium, (sometimes generically referred to as 'paper herein') is loaded along paper load entry direction 302 toward the front 308 of printer chassis 300.

A variety of rollers are used to advance the recording medium through the printer as shown schematically in the side view of FIG. 4. In this example, a pickup roller 320 moves the top sheet 371 of a stack 370 of paper or other recording medium in the direction of arrow 302. A turn roller 322 acts to move the paper around a C-shaped path (in cooperation with a curved rear wall surface) so that the paper continues to advance along direction arrow 304 from the rear 309 of the printer (with reference also to FIG. 3). The paper is then moved by feed roller 312 and idler roller(s) 323 to advance along the Y axis across print region 303, and from there to a discharge roller 324 and star wheel(s) 325 so that printed paper exits along direction 304. Feed roller 312 includes a feed roller shaft along its axis, and feed roller gear 311 is mounted on the feed roller shaft. Feed roller 312 may consist of a separate roller mounted on the feed roller shaft, or may consist of a thin high-friction coating on the feed roller shaft.

The motor that powers the paper advance rollers is not shown in FIG. 1, but hole 310 at the right side 306 of the printer chassis 300 is where the motor gear (not shown) protrudes through in order to engage feed roller gear 311, as well as the gear for the discharge roller (not shown). For normal paper pick-up and feeding, it is desired that all rollers rotate in a forward direction 313. Toward the left side 307, in the example of FIG. 3, there is the maintenance station 330.

Toward the rear 309 of the printer, in this example, is located the electronics board 390, which contains cable connectors 392 for communicating via cables (not shown) to the printhead carriage 200 and from there to the printhead. Also on the electronics board are typically mounted motor controllers for the carriage motor 380 and for the paper advance motor, a processor and/or other control electronics (shown schematically as controller 14 and image processing unit 15 in FIG. 1), for controlling the printing process, and an optional connector for a cable to a host computer.

Also shown in FIG. 4 is backside recording medium sensor 375, which can be used to detect recording medium identification markings on the backside of the top sheet of recording medium 371 prior to printing. The backside of the recording medium is defined as the side of the sheet that is not intended for printing. Specialty recording medium having glossy, luster, or matte finishes (for example), for different quality recording medium may be marked on the backside by the recording medium, manufacturer to identify the recording medium type. While the backside recording medium sensor 375 is shown in FIG. 4 as being located upstream of pickup roller 320, other locations are possible. Typically the backside recording medium sensor 375 consists of a light source (LED) and a photosensor. Light emitted from the LED is reflected from the backside of the top sheet 371 of recording medium and is detected by the photosensor as the recording medium moves past the sensor 375. The light signal reflected from the manufacturer's marking is different from the light signal on the rest of the backside of the recording medium, so that different spacings of identification bars, for example, may be detected as different spacings of peaks or valleys of optical reflectance. While the backside recording medium sensor 375 is configured to work well with print recording medium designed for the printer, a user may use a variety of recording medium from other sources and the backside markings, if any, may not be recognized by the printer. Therefore, it is useful to have another means of distinguishing different recording medium types. Thus, good printing may be provided for generic recording medium of glossy, matte, plain or other types, perhaps not as optimized as recording medium specified by the manufacturer, but still better than if no identification of generic recording medium type had been made.

Figure 5:
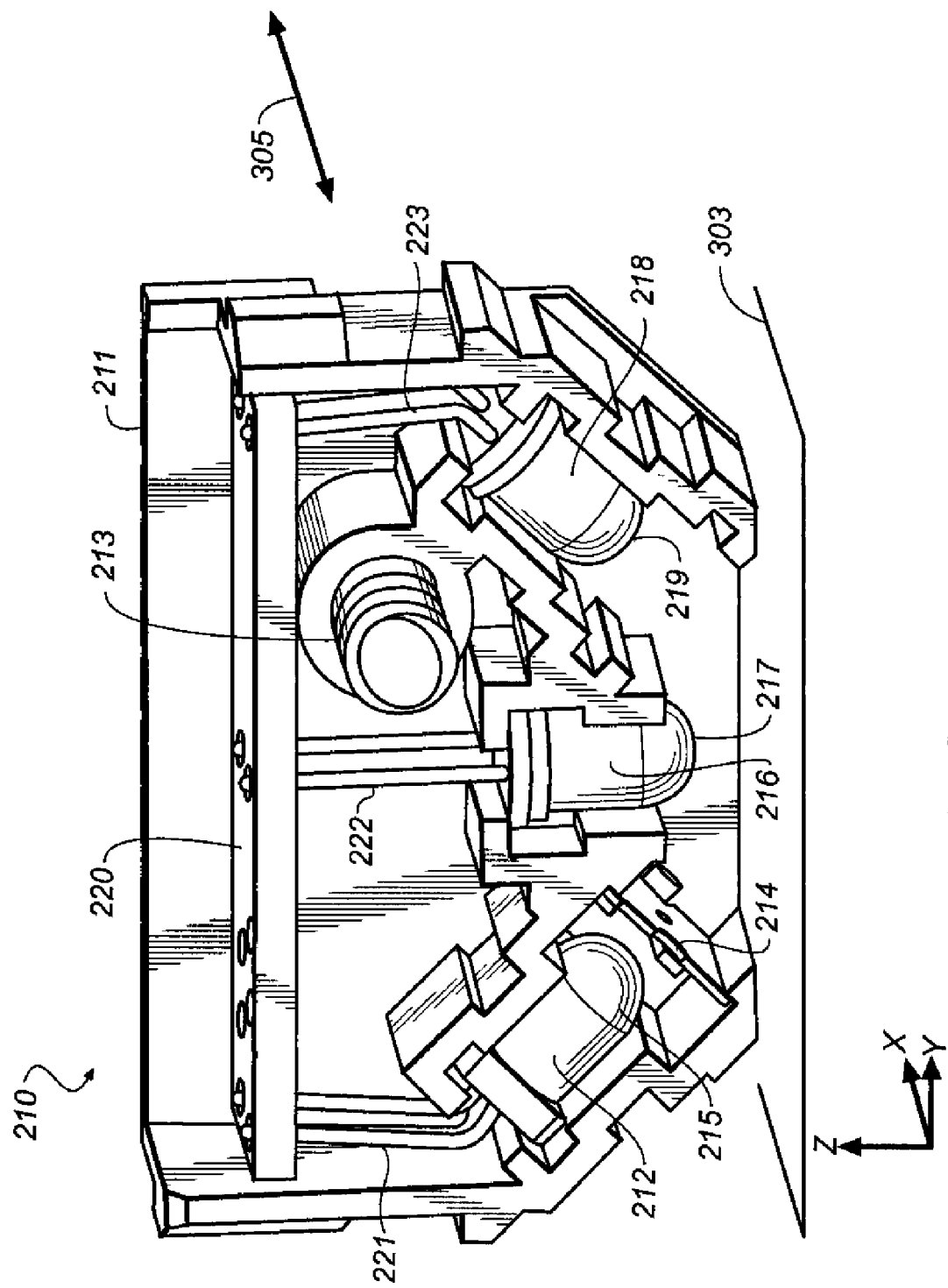
FIG. 5 is a perspective view of a carriage sensor assembly.

FIG. 5 shows a perspective view of the carriage sensor assembly 210, the frame 211 of which may be attached to carriage 200 by bolt 213, for example. Such a carriage sensor assembly 210 and a recording medium detection method using it are disclosed in co-pending U.S. patent application Ser. No. 12/037,970; which is incorporated by reference herein in its' entirety. Also shown in carriage sensor assembly 210 are photosensor 212, aperture 214, first LIED 216 and second LED 218. The photosensor 212 and the two LED's 216 and 218 include semiconductor devices (not shown) that are encapsulated in optically clear materials that form lenses (215, 217, and 219 respectively). Lens 215 helps to focus light received through aperture 214 onto the photosensor device, while lenses 217 and 219 help to direct the emitted light toward the plane of the recording medium.

Electrical leads 221, 222, and 223 from the photosensor 212 and the two LED's 216 and 218 are connected to a wiring board 220, and from the wiring board 220, to leads (not shown) that may be connected to an electronics board (not shown) that is attached to the carriage 200. It is preferable for an amplifier circuit to be physically close to the photosensor 212, because the photosensor output signal is relatively weak and it is important to avoid extraneous electrical noise, for example from printer motor cables, etc. The electronics board attached to carriage 200 may include the electronics for the powering of the LED's and for amplifying the photosensor signal.

FIG. 5 shows an orientation of carriage sensor assembly 210 that is appropriate for a printer, in which the recording medium in the print zone 303 is located horizontally below the printhead 250, and the carriage sensor assembly 210, which are mounted on carriage 200. First LED 216 is oriented to emit light vertically downward, i.e., substantially normal to the plane of the recording medium in the print zone 303. Photosensor 212 is configured to be on one side of first LED 216, and photosensor 212 is oriented to receive light along a direction that is at an angle of about 45 degrees with respect to the normal to the plane of the recording medium (and pointing toward the back of the printer so that it does not receive external stray light) in this example. Second LED 218 is configured to be on the other side of first LED 216, and second LED 218 is oriented to emit light at substantially the same angle with respect to the normal, as the photo sensor 212, but on the other side of the normal. In this example, second LED 218 is oriented to emit light along a direction that is around 45 degrees from the normal to the plane of the recording medium in the print zone. Thus, the two LED's are configured relative to the photosensor in this example such that the photosensor 212 receives specular reflections of light incident on the recording medium from second LED 218, and photosensor 212 receives diffuse reflections of light incident on the recording medium from first LED 216. Photosensor 212 provides an output signal (typically an output current) corresponding to the amount of light that strikes the photosensor 212.

Aperture 214 determines the range of angles of incident light rays that are able to pass to the photosensor 212, while the opaque region around the aperture blocks light rays outside this range of angles. The region of the recording medium that the photosensor "sees" depends not only on the geometry of the aperture, but also upon its orientation relative to the plane of the recording medium. This region that the photosensor "sees" will also herein be called the photosensor's field of view. In the example shown in FIG. 5, where the axes of the photosensor 212 and the aperture 214 are inclined relative to the Y direction (where Y is the recording medium advance direction), the field of view of photosensor 212 through aperture 214 will be somewhat elongated along the Y direction even if the physical shape of the aperture 214 is circular. For a typical spacing of carriage sensor assembly 210 to the paper in print zone 303, an aperture having an oval shape of dimensions 0.5 mm by 0.3 mm may provide a photosensor field of view of around 3.0 mm along Y by 1.5 mm along X.

It is found that the signal received in photosensor 212 from specular reflections of light emitted from LED 218, is highly sensitive to the shape of the surface of the recording medium, and can be used as a means to detect generic paper types (such as glossy photo paper, matte photo paper, and plain paper) by the characteristics of the noise in the photosensor signal from an unmarked printing surface of recording medium. Unlike backside recording medium sensor 375, which can detect recording medium type as it is being fed from the paper tray, the carriage sensor assembly 210 cannot detect generic paper type until the recording medium has reached print zone 303. If the backside recording medium sensor 375 has not identified a specific paper type, the carriage sensor assembly 210 may be used. In particular, the specular LED 218 emits light (and not diffuse LED 216), while scanning across the recording medium prior to the printhead beginning its print job, and the signal is analyzed to determine the paper type, so that the proper data rendering can be done in image processing unit 15 for good image quality on that paper type. The choice of wavelength of the specular LED 218 is not critical, but can be blue, for example.

The photosensor signal is typically amplified electronically, and the amplified signal is sent to an analog to digital converter (ADC) to provide a set of digital data. Optionally, the DC component of the electronic signal is filtered out and the signal is biased prior to analog to digital conversion so that the resulting signal is roughly centered in the range of the ADC, thereby making efficient use of the range.

Figure 6A:
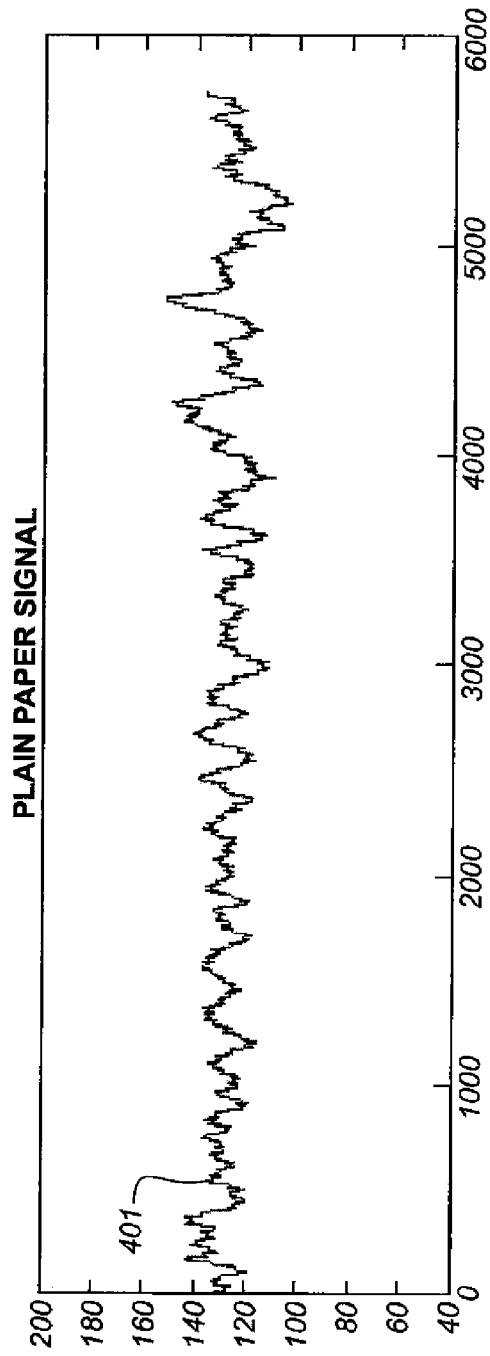
FIGS. 6A and 6B show examples of digitized data from an amplified photosensor signal corresponding to plain paper and glossy photo paper.
Figure 6B:
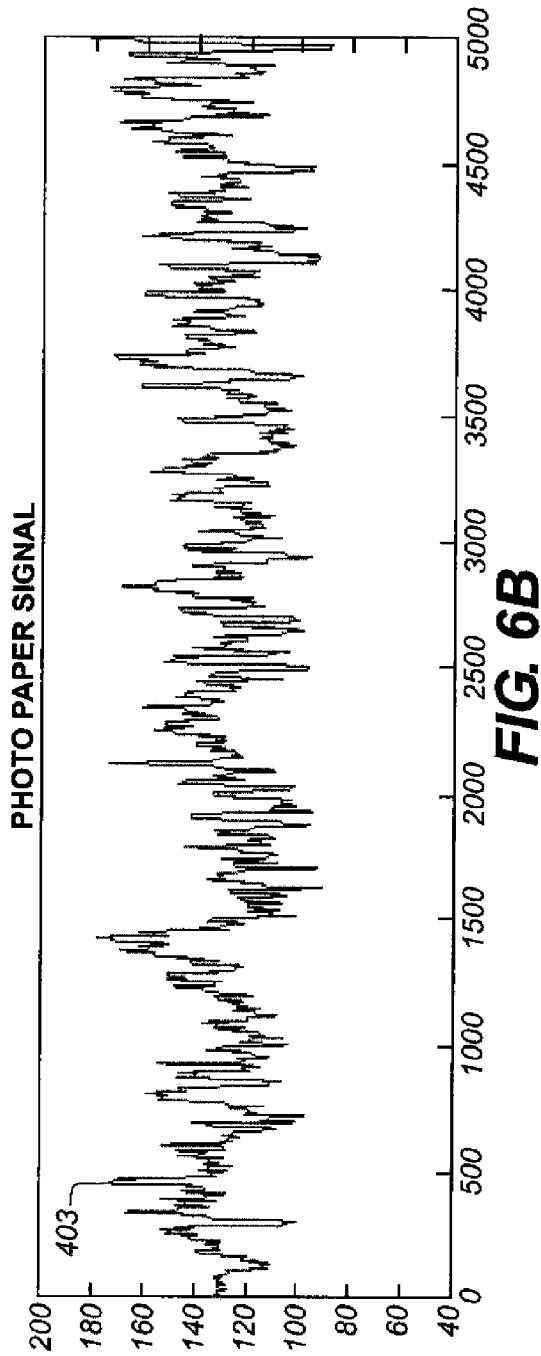

FIGS. 6A and 6B show examples of data from the ADC for representative samples of plain paper (plot 401 in FIG. 6A) and glossy photo paper (plot 403 in FIG. 6B). Note that for each plot, the Y-axis values of the data are centered around the mid-range of 8-bit ADC (level 128), as described above. The X-axis values of the data represent the position on the recording medium as the field of view of the photosensor 212 is scanned across the recording medium. The horizontal position can be related to a time-varying photosensor signal by scanning the photosensor 212 at a constant velocity such as 10 inches per second. Optionally, the horizontal coordinates of the photosensor signal can be correlated with spatial position on the recording medium through the encoder fence 383, as detected by an encoder sensor mounted on carriage 200. The actual position of the field of view relative to the recording medium is not used in the calculations described below, but the spatial ordering of data from photosensor 212 is preserved. In other words, neighboring data points in a digitized data set $D_n$ and $D_{n+1}$ represent positions on the recording medium that are spatially closer together than the positions represented by other data points $D_n$ and $D_{n+2}$.

As is readily apparent from FIGS. 6A and 6B, the signal 401 from plain paper has relatively high amplitude of low frequency variations, but relatively low amplitude of high frequency variations. By comparison, signal 403 from glossy photo paper is dominated by high amplitude high frequency variations. Many different specific papers classified into these generic paper types were measured and were found to have similar trends relative to amplitudes of high frequency and low frequency variations in the signal.

During scanning of the recording medium, the photosensor sampling rate is set to 25 kHz, for example, as the carriage moves at 10 inches per second, thus providing specular reflection data from the recording medium at a resolution of 2500 data points per inch. The digitized data from the ADC is typically stored in memory for further processing. To improve the signal to noise ratio and reduce the data processing load, the digitized data can be summed or averaged over a plurality (such as five) of data samples from the ADC and related to each encoder reading. In order to further reduce high frequency noise in the data, a moving average of the data can subsequently be calculated.

A central aspect of the present invention is a method for analyzing the frequency distribution of the (optionally smoothed) digital data. Embodiments of this method include summing a first series of terms, where the terms include a plurality of data points that are spaced apart from one another by a first spacing, and comparing the magnitude of the sum of the first series to the sum of a second series of terms, where the terms of the second series include a plurality of data points that are spaced apart from one another by a second spacing. The comparison of the magnitudes of the sums is then correlated with known characteristics of magnitudes of such sums that are stored in printer memory in order to identify the type of recording medium.

Figure 7:
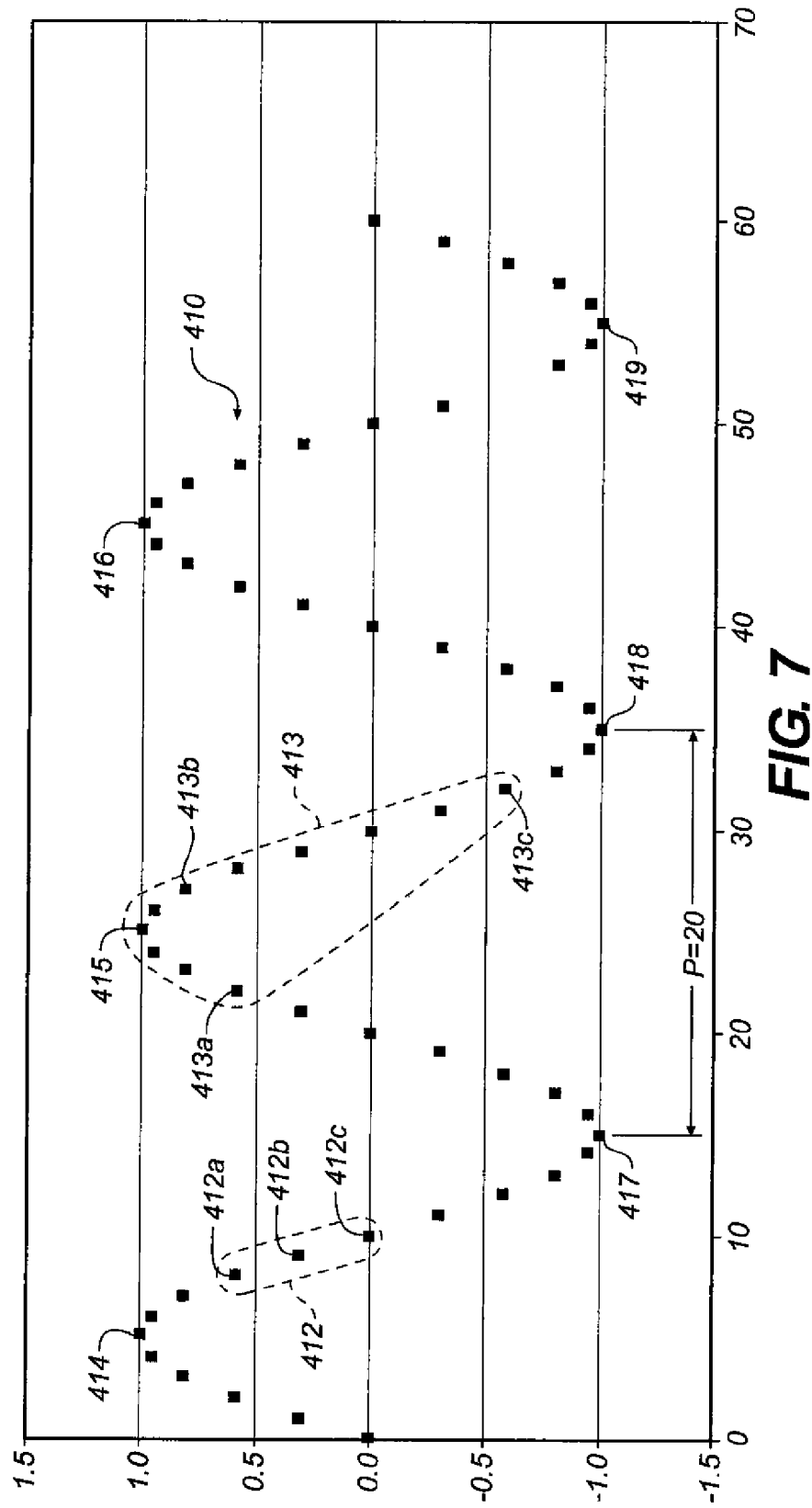
FIG. 7 is a set of data points for a sine wave having a period of 20.
Figure 8:
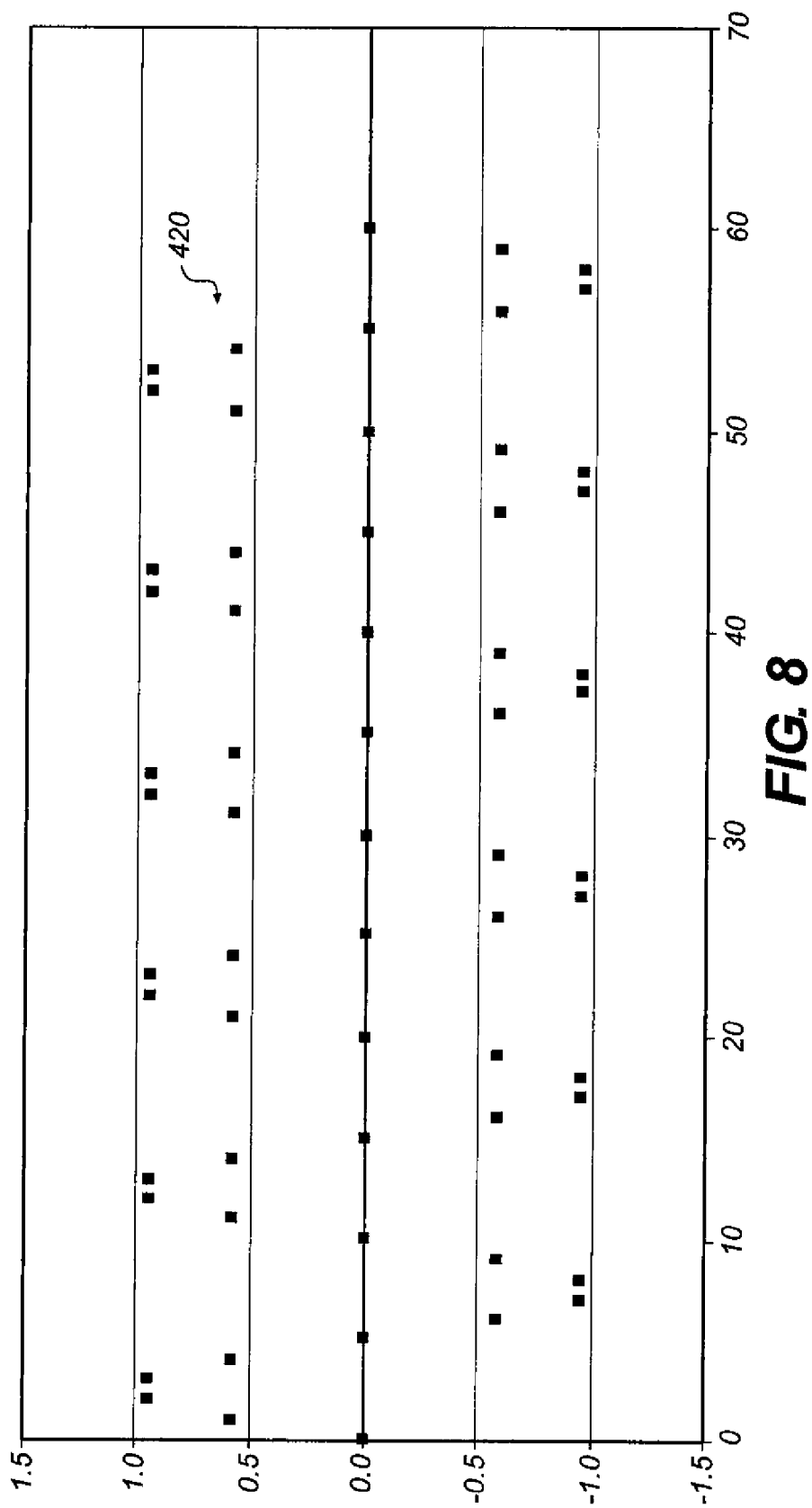
FIG. 8 is a set of data points for a sine wave having a period of 10.

An embodiment of the method will be described with respect to a simple example of sine waves of two different frequencies, in order to clarify how the analysis of the frequency distribution works. FIG. 7 shows the first sixty data points for a sine wave 410 having a period of twenty data points, so that there are three complete cycles shown in the figure. The equation for the $n^{th}$ data point $D_n$ for a sine wave having a period of P data points is $D_n=\sin(2\pi n/P)$, so the equation for curve 410 is $D_n=\sin(\pi n/10)$. The FIG. 8 shows the first sixty data points for a sine wave 420 having an equation $D_n=\sin(\pi n/5)$ and a period of ten data points, so that there are six complete cycles shown in the figure. The period of sine wave 420 is half of the period of sine wave 410. Correspondingly, the frequency of sine wave 420 is twice the frequency of sine wave 410.

Different groupings of data points are shown in FIG. 7 in order to clarify the concept of data point spacing. In data point grouping 412, the three data points are adjacent to one another. In the data set making up sine wave 410, data point 412a is the ninth data point from the beginning of the data set (counting from the left) at $D_0$, so data point 412a is $D_8$. Data point 412b is $D_9$ and data point 412c is $D_{10}$. Data point 412a is said to have a data spacing of 1 with respect to data point 412b and a data spacing of 2 with respect to data point 412c. In data point grouping 413, the two outside data points 413a and 413c each have a data spacing of 5, with respect to data point 413b, which is midway between them. Equal spacing of data points, in this regard, does not mean equal spacing of the values of the data points, but of the spacing of the data points in the data set.

In one exemplary embodiment of the invention, a series of terms is summed in order to provide a magnitude $F_L$, in which the spacing of the data points in the terms is L. In particular, in this embodiment:

$$F_L = \text{Sum}[\text{absolute value}(D_i + D_{i+2L} - 2D_{i+L})] \quad \text{(Equation 1)}$$

In computing magnitude $F_1$ for sine wave 410 (shown in FIG. 7), for example, one of the terms would include the three terms from grouping 412 that have a spacing of one relative to each other, and would be: [absolute value $(D_8+D_{10}-2D_9)$]. Similarly in computing magnitude $F_5$ for sine wave 410, one of the terms would be from grouping 413 that have a spacing of five relative to each other, and would be: [absolute value $(D_{22}+D_{32}-2D_{27})$].

In practice, the summations of a series of data points could include on the order of a thousand or more terms. The magnitudes $F_1, F_2, \ldots F_{20}$ were calculated according to Equation 1 above, for data sets having the form of sine waves 410 and 420 (shown in FIG. 8) where each summation included 1000 terms. This requires a data set of over 1000 data points because the $i^{th}$ term includes not only the $i^{th}$ data point, but also the $(i+2L)^{th}$ data point. For example, 1040 data points are needed to calculate 1000 terms for $F_{20}$. Results for the calculations are provided in Table 1 below:

TABLE 1

| Data point spacing L | $F_L$ for $\sin(\pi n/5)$<br>P = 10 | $F_L$ for $\sin(\pi n/10)$<br>P = 20 |
|---|---|---|
| 1 | 235.1 | 61.8 |
| 2 | 850.7 | 241.2 |
| 3 | 1611.5 | 520.5 |
| 4 | 2227.0 | 872.5 |
| 5 | 2462.1 | 1262.8 |
| 6 | 2227.0 | 1653.0 |
| 7 | 1611.5 | 2005.0 |
| 8 | 850.7 | 2284.3 |
| 9 | 235.1 | 2463.7 |
| 10 | 0.0 | 2525.5 |

| Data point spacing L | FL for $\sin(\pi n/5)$<br>P = 10 | FL for $\sin(\pi n/10)$<br>P = 20 |
|---|---|---|
| 11 | 235.1 | 2463.7 |
| 12 | 850.7 | 2284.3 |
| 13 | 1611.5 | 2005.0 |

TABLE 1-continued

| 14 | 2227.0 | 1653.0 |
|---|---|---|
| 15 | 2462.1 | 1262.8 |
| 16 | 2227.0 | 872.5 |
| 17 | 1611.5 | 520.5 |
| 18 | 850.7 | 241.2 |
| 19 | 235.1 | 61.8 |
| 20 | 0.0 | 0.0 |

As can be seen from Table 1, the values of $F_L$ are periodic, such that for L=P, the magnitude $F_P=0$; and for L=P/2, the magnitude $F_{P/2}$ is the maximum value of $F_L$. Furthermore, for both P=10 and P=20, the maximum value of $F_L$ is about 2500. This is due to calculating magnitudes for sine waves, as will be explained below.

First of all, referring to FIG. 7: points 414 (n=5), 415 (n=25), and 416 (n=45) are located at peaks of the data set; and points 417 (n=15), 418 (n=35), and 419 (n=55) are located at valleys of the data set for sine wave 410. For a data point spacing L that is equal to the period P (i.e., L=20 in FIG. 7); it is obvious that since the data points 414, 415, and 416 all have a value of 1, the term of the sum: [absolute value $(D_5+D_{45}-2D_{25})$]=0. In fact, for a spacing of L=P, every term in the sum equals 0, as does the sum $F_P$ itself. For a data point spacing that is half the period (L=P/2), one particular term for P=20 and L=10 is for points 414, 417, and 415, such that the term of the sum is [absolute value $(D_5+D_{25}-2D_{15})$]=1+1−(−2)=4. Similarly another term is [absolute value $(D_{15}+D_{35}-2D_{25})$] absolute value [(−1)+(−1)−(2)]=4.

Use of the trigonometric relationship:

$$\sin(\alpha+\beta)=(\sin\alpha\cos\beta)+(\cos\alpha\sin\beta)$$

provides a more general way to calculate some magnitudes at particular data point spacings. Expressing β in radians:

if β=2π (i.e., a full period); then $\sin(\alpha+\beta)=\sin\alpha$;

if β=π (i.e., half a period); then $\sin(\alpha+\beta)=-\sin\alpha$; and if β=π/2 (i.e., one quarter a period); then $\sin(\alpha+\beta)=\cos\alpha$.

For L=P, the $n^{th}$ term of the sum $F_P$ has the form:

absolute value$[\sin(2\pi n/P)+\sin(2\pi n/P)-2\sin(2\pi n/P)]$
=0;

so the entire sum $F_P=0$ as stated above.

For L=P/2, the $n^{th}$ term of the sum $F_{P/2}$ has the form:

absolute value$[\sin(2\pi n/P)+\sin(2\pi n/P)-(-2\sin(2\pi n/P))]$= absolute value$[4\sin(2\pi n/P)]$

If there are N terms in the sum, then the magnitude of $F_{P/2}$ is equal to 4N times the average of the absolute value of $\sin(2\pi n/P)$. If P is much larger than 1, then a good approximation of the average of the absolute value of $\sin(2\pi n/P)$ is given by integrating over the positive half cycle and dividing by half the period. In particular, integrating from 0 to π:

$$\int \sin(2\pi x/P)dx = -(P/2\pi)(\cos(\pi)-\cos(0))=P/\pi$$

Dividing this result by half the period, i.e. by P/2, gives 2/π as the average of the absolute value of $\sin(2\pi n/P)$. Thus, if there are N=1000 terms in the sum $F_{P/2}$, a good approximation (for P much greater than 1) is $F_{P/2} \approx 4N(2/\pi)=8000/\pi \sim 2546$. As can be seen in Table 1 above, $F_{P/2}$ for P=10 was calculated to be 2462, while $F_{P/2}$ for P=20 was calculated to be 2526, which is within 1 percent of the approximate value of 4N (2/π). As can be seen, the magnitude $F_{P/2}$ is independent of the period P, other than the fact that the approximation is better for larger P.

Similarly it can be shown that a good approximation for $F_{P/4}$ (for P much greater than 1) is given by $F_{P/4}$~4N/π~1273 if there are N=1000 terms. In Table 1 for P=20, $F_{P/4}$ was calculated to be 1263, which is within 1 percent of the approximate value of 4N/π. For P=10 there is no integer value for P/4=2.5, so there is not a corresponding magnitude near 1273, although the average of the magnitudes $F_2$ and $F_3$ (i.e., 1231) is not far off.

In general, it is found for a data set having points given by: $D_n$=sin(2πn/P), the magnitude $F_L$ for data point spacing L, where $F_L$ is given by equation 1 above, is:

$$F_L \sim (4N/\pi)(1-\cos(2\pi L/P)) \qquad \text{(Equation 2)}$$

Figure 9:
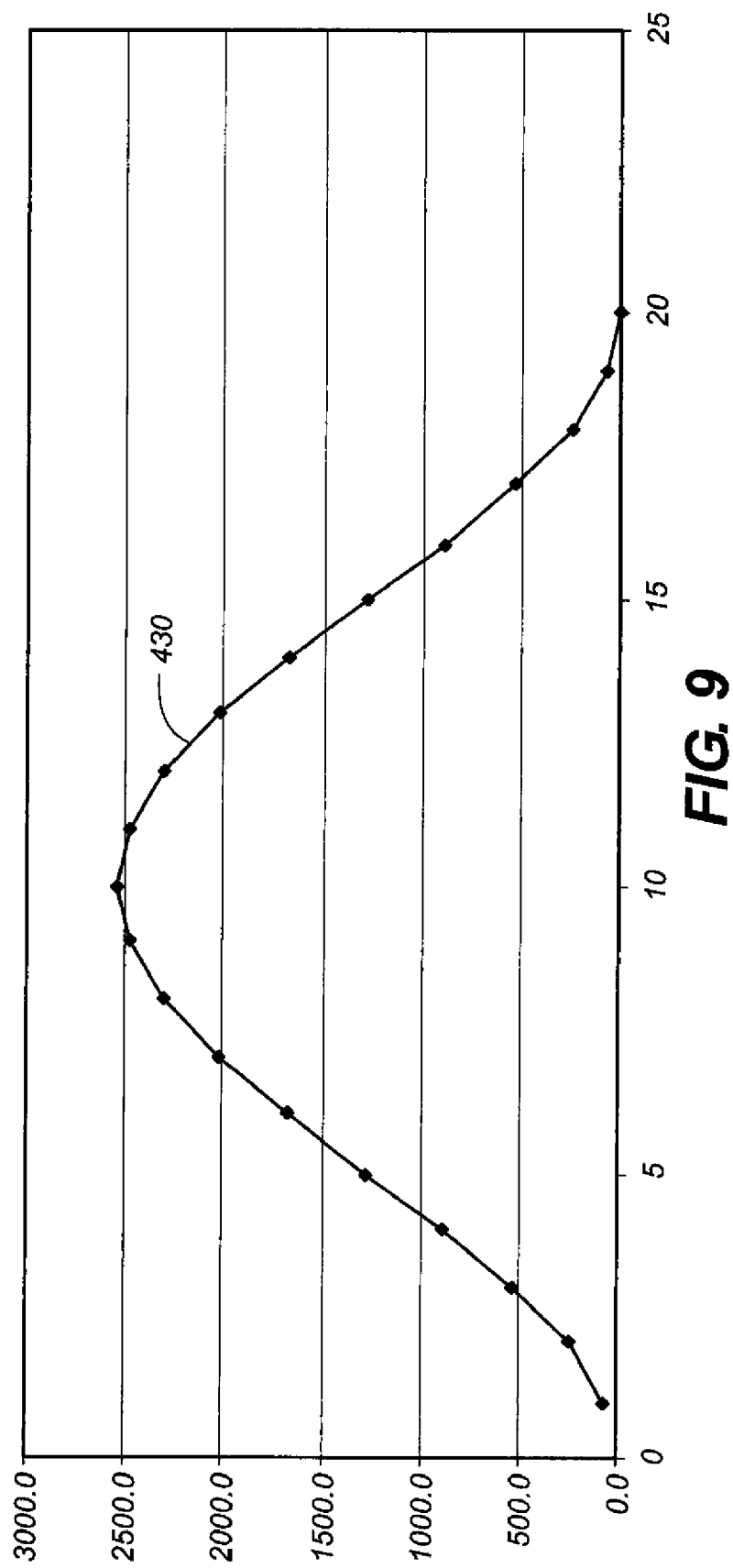
FIG. 9 is a fitted plot for the magnitudes of sums of terms having different data spacings for a sine wave having a period of 20.
Figure 10:
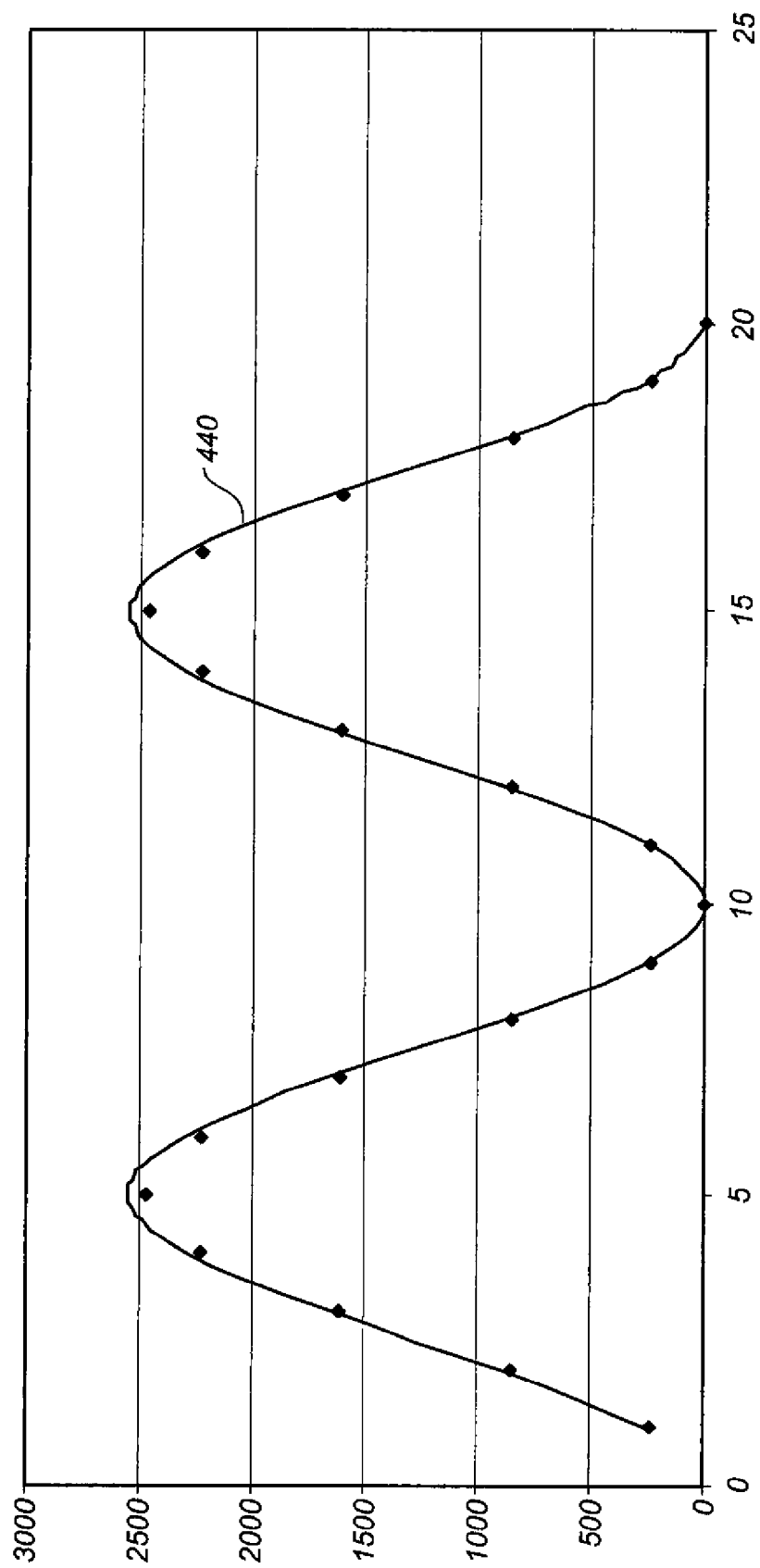
FIG. 10 is a fitted plot for the magnitudes of sums of terms having different data spacings for a sine wave having a period of 10.

In FIG. 9, the magnitudes $F_L$ from Table 1 for P=20 and N=1000 are plotted as points, while equation 2 is plotted as a curve 430. The horizontal axis is the spacing L. The fit of curve 430 is very good. In FIG. 10, the magnitudes $F_L$ from Table 1 for P=10 and N=1000 are plotted as points, while equation 2 is plotted as a curve 440. The fit of Equation 2 in FIG. 10 is not quite as good as for the larger value of P in FIG. 9, but it is still a good fit.

Actual data sets corresponding to photosensor data for specular reflection from plain paper and photo paper, as shown by examples in FIGS. 6A and 6B respectively, are much more complex than pure sine waves. The data sets in FIGS. 6A and 6B are not periodic, they do not have the same amplitude of variation, and they have components of variation both at high frequency and at low frequency. Still, it can be observed that a sum of the form of Equation 1 provides a measurement of the amount of curvature that exists between the data points $D_i$ and $D_{i+2L}$. This is because if the three data points in a term of Equation 1 were in a straight line, that term would equal zero. Therefore, for small values of data spacing L, data sets that are dominated by variation at high frequency (having a lot of curvature even at small spacing of the data points) tend to have a higher magnitude of $F_L$ than data sets that are dominated by variation at low frequency. For larger values of data spacing L, data sets that are dominated by variation at low frequency tend to have a higher magnitude of $F_L$ than data sets that are dominated by variation at high frequency. However, this is complicated in that for large enough values of L (greater than P/2 for the case of a sine wave of period P), $F_L$ begins to decrease.

Calculation of magnitudes $F_L$ of a few sums of the form of Equation 1 can thus be used as a simple and fast way to distinguish between sets of photosensor data corresponding to plain paper (characterized predominantly by low frequency variation) and sets of photosensor data corresponding to photo paper (characterized predominantly by high frequency variation). The details of how the various magnitudes $F_L$ are compared depends on factors such as the spatial frequency of the data sampling of the photosensor relative to the spatial frequency inherent in the recording medium, as well as any preprocessing of the digitized data (such as summing, averaging, or computing a moving average) that is done prior to calculating $F_L$. The comparison may be as simple as checking whether $F_{L1}$>A$F_{L2}$, where A is a constant and spacing L1 is not equal to spacing L2 (i.e., comparing two magnitudes of sums where the data points for the terms of one sum have a different spacing than the data points for the terms of the other sum). Other methods of comparison can be more complex in order to provide a more reliable distinction between types of recording medium.

Figure 11:
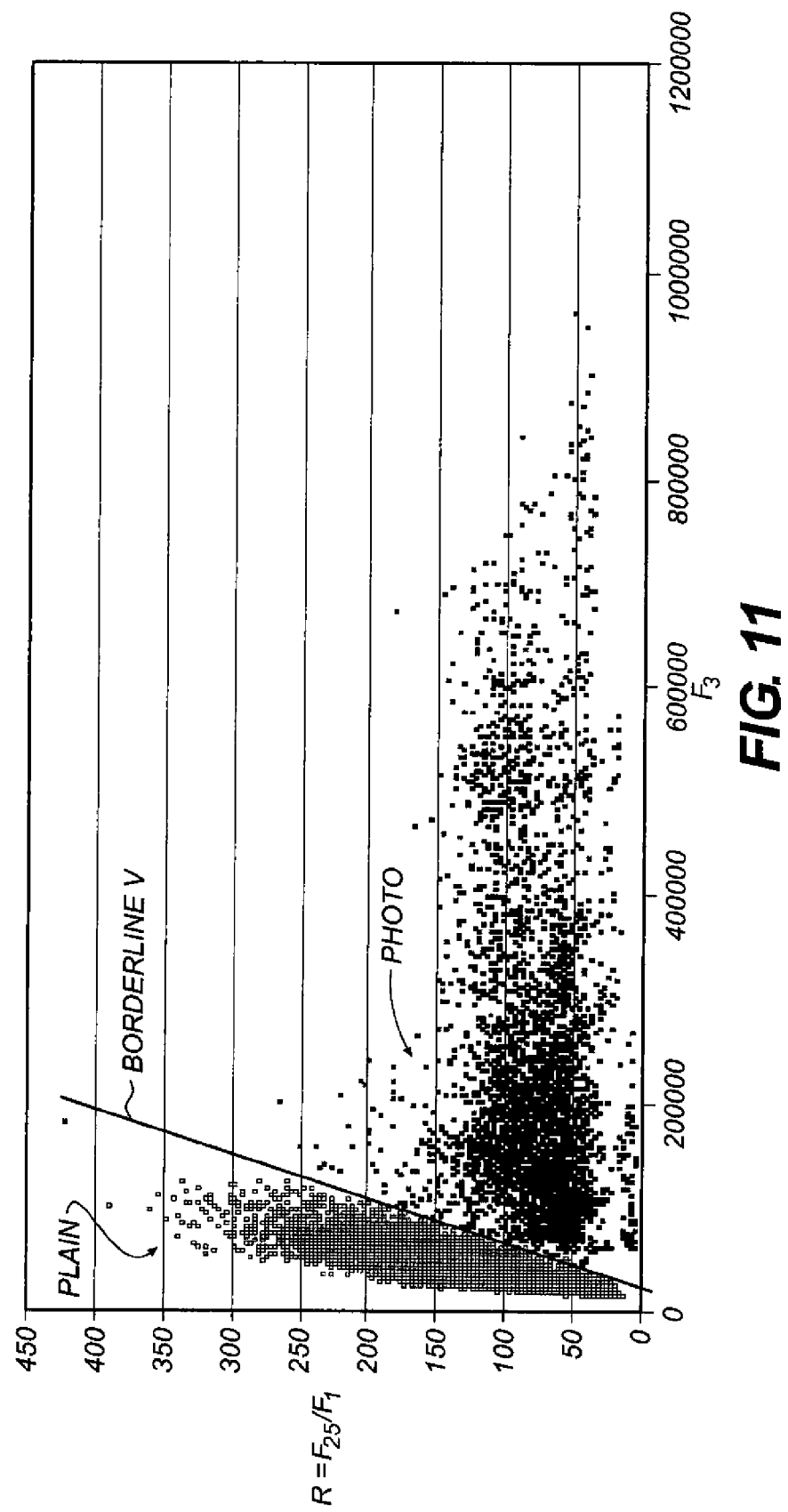
FIG. 11 is a graphical representation of an embodiment of the present invention for distinguishing between photo paper and plain paper.

In one embodiment ten different printers having nominally equivalent carriage sensor assemblies 210 were used to characterize twenty six different recording medium types, with two repeats of each recording medium type per printer. This provided 26×20=520 different data sets to analyze. Three magnitudes of $F_L$ ($F_1$, $F_3$ and $F_{25}$) were computed for each of the 520 data sets. It was found that comparing the ratio R=$F_{25}$/$F_1$ (which tends to be large for low frequency data sets corresponding to typical plain papers) with a borderline V given by the linear equation of V=250($F_3$−38000)/60000=250 $F_3$−158.3, if R>V the recording medium can be identified as plain paper, and if R<V the recording medium can be identified as photo paper. This method of distinguishing recording medium types was found to be about 99 percent accurate, as is shown by the graph of data points in FIG. 11. The linear function V and the ratio R are two examples of types of functions that can be used in comparing magnitudes of sums of data points having different spacings, but other types of functions could also be used. A piecewise linear function V consisting of a plurality of linear functions of some magnitude $F_L$ joined end to end in different regions could alternatively be used as the borderline to distinguish between two types of recording medium.

Figure 12A:
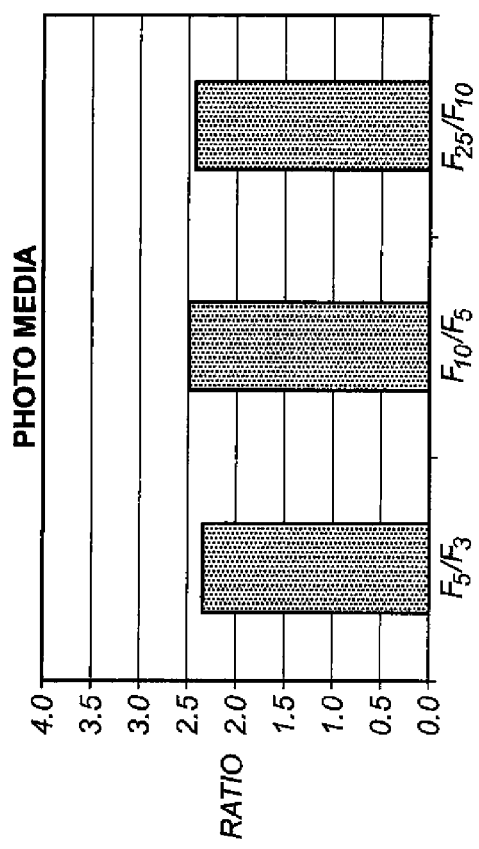
FIGS. 12A and 12B are a graphical representation of an embodiment of the present invention for distinguishing between photo paper and plain paper.
Figure 12B:
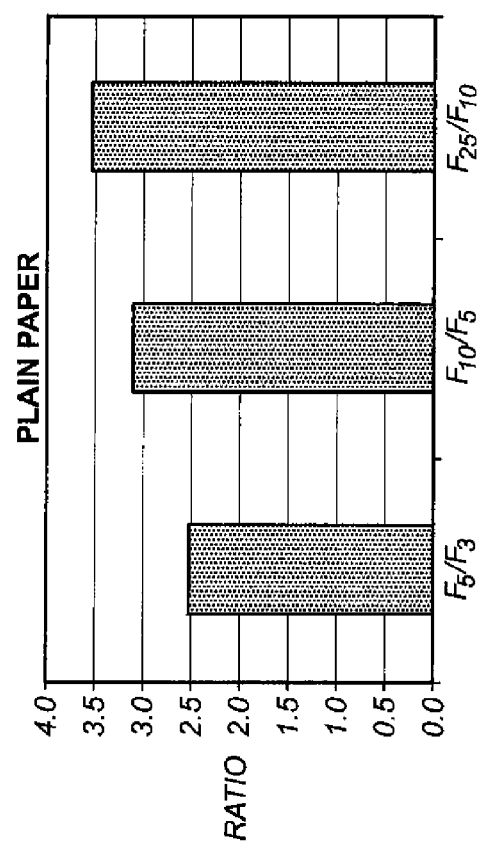

An alternative way to identify recording medium type is to observe the trends of the ratios $R_1$=$F_5$/$F_3$, $R_2$=$F_{10}$/$F_5$, and $R_3$=$F_{25}$/$F_{10}$. For photo recording medium it is found in one embodiment that $R_1$~$R_2$~$R_3$, as shown in FIG. 12A. However, in this same embodiment it is found that for plain paper, $R_3$>$R_2$>$R_1$, as shown in FIG. 12B.

Furthermore, it has been found that the accuracy of identification of plain paper versus photo paper is improved by using more than one comparison of magnitudes $F_L$ (for example, the comparison described above with reference to FIG. 11 and another comparison using a different combination of magnitudes and borderlines). Even if some recording medium will be on the wrong side of the borderline in one comparison, they will be on the right side of the borderline (and far from the borderline) in another comparison. By using plurality of comparisons of magnitudes $F_L$, a more accurate identification can be made.

It has also been shown that an embodiment of the present invention is more robust against changes in external conditions or manufacturing variation than an embodiment of the method described in commonly assigned U.S. patent application Ser. No. 12/037,970. A way to characterize robustness is to change the intensity of the illumination from LED 218 and see how much change can be tolerated by the various methods for accurate recording medium identification. Intensity of illumination of an LED can be varied through pulse width modulation of the voltage applied to the LED, for example. It was found that an embodiment of the present invention could tolerate a change of ±7 counts of pulse width modulation, while an embodiment of the method described in U.S. patent application Ser. No. 12/037,970 could tolerate a change of ±3 counts of pulse width modulation. Therefore, the improved robustness of the method of the present invention is demonstrated.

In the embodiments above, Equation 1 has been used to determine the magnitudes of the sums of terms of data points having various spacings between data points. However, the method is not restricted to the use of Equation 1. In particular, it is contemplated that the absolute value of each term could be replaced by the square of each term, or other functions of each term in other embodiments. For comparing magnitudes of different sums where the data points have different spacings, the functions for the different sums could be the same functions, or they could be differing functions. In addition, it is not required that for sums involving three data points, the data points be equally spaced as in the previous embodiments.

More generally, embodiments of the present invention include computing a first summation $S_1=\text{Sum}[f_1(a_1D_i-b_1D_j+c_1D_k)]$ and a second summation $S_2=\text{Sum}[f_2(a_2D_l-b_2D_i+c_2D_m)]$, and comparing the two sums in order to identify a type of recording medium. In the notation of these expressions: $a_1$, $b_1$, $c_1$, $a_2$, $b_2$, and $c_2$, are all numerical constants greater than zero; i, j, k, l, and m are integer values such that: k>j>i, m>l>i; m>k, and m>j; and $f_1$ and $f_2$ are functions. Functions $f_1$ and $f_2$ can be the same function as each other. In Equation 1, $f_1$ and $f_2$ are both the absolute value function. Also, in Equation 1, $a_1=a_2=c_1=c_2=1$, and $b_1=b_2=2$.

The invention has been described in detail with particular reference to certain preferred embodiments thereof, but it will be understood that variations and modifications can be effected within the spirit and scope of the invention. In particular, the scope of this present invention of a method for analyzing and comparing frequency distributions can be extended beyond identifying types of recording medium. Another use of such a method includes identifying a type or quality of sheet goods (such as plywood or lumber) being transported on a conveyor belt past a photosensor according to variations in the woodgrain or other surface characteristic of the sheet goods or body being transported. The method can also be extended to analysis of audio signals received by a microphone. For example, the method could be used to distinguish a baby's cry from a dog's bark in a baby monitoring device.

The invention has been described in detail with particular reference to certain preferred embodiments thereof, but it will be understood that variations and modifications can be effected within the spirit and scope of the invention.

PARTS LIST

10 Inkjet printer system
12 Image data source
14 Controller
15 Image processing unit
16 Electrical pulse source
18 First fluid source
19 Second fluid source
20 Recording medium
100 Inkjet printhead
110 Inkjet printhead die
111 Substrate
120 First nozzle array
121 Nozzle in first nozzle array
122 Ink delivery pathway for first nozzle array
130 Second nozzle array
131 Nozzle in second nozzle array
132 Ink delivery pathway for second nozzle array
181 Droplet ejected from first nozzle array
182 Droplet ejected from second nozzle array
200 Carriage
210 Carriage sensor assembly
211 Frame of carriage sensor assembly
212 Photosensor
213 Bolt
214 Aperture
215 Photosensor lens
216 LED mounted for diffuse reflections
217 LED lens
218 LED mounted for specular reflections
219 LED lens
220 Wiring board
221 Photosensor electrical leads
222 LED electrical leads
223 LED electrical leads
250 Printhead chassis
251 Printhead die
253 Nozzle array
254 Nozzle array direction
256 Encapsulant
257 Flex circuit
258 Connector board
262 Multichamber ink supply
264 Single chamber ink supply
300 Printer chassis
302 Paper load entry
303 Print region
304 Paper exit
306 Right side of printer chassis
307 Left side of printer chassis
308 Front of printer chassis
309 Rear of printer chassis
310 Hole for paper advance motor drive gear
311 Feed roller gear
312 Feed roller
313 Forward rotation of feed roller
320 Pickup roller
322 Turn roller
323 Idler roller
324 Discharge roller
325 Star wheel
330 Maintenance station
370 Stack of recording medium
371 Top sheet
375 Backside recording medium sensor
380 Carriage motor
382 Carriage rail
383 Encoder fence
384 Belt
390 Printer electronics board
392 Cable connectors
401 Signal corresponding to plain paper
403 Signal corresponding to glossy photo paper
410 Sine wave data with period of 20
412 Grouping of data points with spacing of 1
413 Grouping of data points with spacing of 5
420 Sine wave data with period of 10

What is claimed is:

1. A method for analyzing frequency distribution of a reflection from a surface of a body to determine a type of body surface, the method comprising the steps of:

providing a plurality of data points from a sensor that senses the reflection of the body's surface;

summing a first series of terms to provide a first magnitude, each term including a plurality of data points, wherein the plurality of data points being spaced apart by a first spacing;

summing a second series of terms to provide a second magnitude, each term including a plurality of data points, wherein the plurality of data points being spaced apart by a second spacing; and comparing the first magnitude to the second magnitude to determine the type of body surface.

2. The method claimed in claim 1, further comprising the step of:

a) summing a third series of terms to provide a third magnitude, each term including a plurality of data points, wherein the plurality of data points being spaced apart by a third distinct spacing different from either first or second spacing.

3. The method claimed in claim 2, wherein the step of comparing the first magnitude to the second magnitude includes:
 a) computing a function of the first magnitude;
 b) computing a function of the second and third magnitude; and
 c) determining whether the function of the first magnitude is greater than the function of the second and third magnitude.

4. The method claimed in claim 3, wherein the function of the first magnitude is a linear function.

5. The method claimed in claim 4, wherein the function of the second and third magnitude is a ratio.

6. The method claimed in claim 2, further comprising the step of:
 a) summing a fourth series of terms to provide a fourth magnitude, each term including a plurality of data points, wherein the plurality of data points being spaced apart by a fourth distinct spacing different from either first, second, or third spacing.

7. The method claimed in claim 6, wherein the step of comparing the first magnitude to the second magnitude includes:
 a) computing a function of the first and third magnitude;
 b) computing a function of the second and fourth magnitude; and
 c) determining whether the function of the first and third magnitude is greater than the function of the second and fourth magnitude.

8. A method for identifying a type of recording medium using a time-varying output signal from a photosensor, the method comprising the steps of:
 converting the time varying output signal of the photosensor to digitized data points using an analog to digital converter thereby creating a set of digitized data points $D_n$, where neighboring data points $D_n$ and $D_{n+1}$ represent positions on the recording medium that are spatially closer together than the positions represented by data points $D_n$ and $D_{n+2}$;
 computing a first summation $S_1 = \text{Sum}[f_1(a_1 D_i - b_1 D_j + c_1 D_k)]$, where:
 $f_1$ is a first function;
 $a_1$, $b_1$, and $c_1$ are all greater than zero;
 i, j, and k are integer values of n such that k>j>i; and
 computing a second summation $S_2 = \text{Sum}[f_2(a_2 D_i - b_2 D_l + c_2 D_m)]$,
 where:
 $f_2$ is a second function;
 $a_2$, $b_2$, and $c_2$ are all greater than zero;
 i, l, and m are integer values of n such that m>l>i, m>k, and l>j; and
 identifying the recording medium type by comparing $S_1$ and $S_2$.

9. The method of claim 8, wherein the function $f_1$ and the function $f_2$ are the same function.

10. The method of claim 9, wherein the functions $f_1$ and $f_2$ are the absolute value function.

11. The method of claim 8, wherein $a_1 = a_2 = c_1 = c_2 = 1$, and $b_1 = b_2 = 2$.

12. The method of claim 8, wherein j=i+p, k=i+2p, l=i+q, m=i+2q, and q is an integer greater than p.

13. The method of claim 8, further comprising the step of computing a ratio of $S_1$ and $S_2$.

14. The method of claim 8, further comprising the step of performing a moving average of data points before computing summations $S_1$ and $S_2$.

15. The method of claim 8, wherein the time-varying output signal is provided by specularly reflecting light from the surface of the recording medium as the photosensor is moved at a substantially constant speed relative to the recording medium.

16. A method for identifying a type of recording medium using a time-varying output signal from a photosensor, the method comprising the steps of:
 converting the time varying output signal of the photosensor to digitized data points using an analog to digital converter thereby creating a set of digitized data points $D_n$, where neighboring data points $D_n$ and $D_{n+1}$ represent positions on the recording medium that are spatially closer together than the positions represented by data points $D_n$ and $D_{n+2}$;
 computing a first magnitude $F_L$ having terms of spacing L, the first magnitude $F_L$ being computed by the formula;
 $F_L = \text{Sum}[\text{absolute value}(D_i + D_{i+2L} - 2D_{i+L})]$, where i is an integer value of n and L is an integer;
 computing a second magnitude $F_M$ having terms of spacing M, the first magnitude $F_M$ being computed by the formula;
 $F_M = \text{Sum}[\text{absolute value}(D_i + D_{i+2M} - 2D_{i+M})]$, where i is an integer value of n and M is an integer not equal to L; and
 identifying the recording medium type by comparing $F_L$ and $F_M$.

17. The method of claim 16, further comprising the step of:
 computing a third magnitude $F_P$ having terms of spacing P, the first magnitude $F_P$ being computed by the formula;
 $F_P = \text{Sum}[\text{absolute value}(D_i + D_{i+2P} - 2D_{i+P})]$, where i is an integer value of n and P is an integer not equal to either L or M; and
 wherein the step of identifying the recording medium type further comprises comparing $F_L$, $F_M$, and $F_P$.

18. The method of claim 17, wherein the step of identifying the recording medium type further comprises:
 computing the value of $V = AF_P + B$, where A and B are predetermined constants;
 computing the ratio $R = F_L/F_M$; and
 determining whether V>R.

19. The method of claim 16, further comprising the steps of:
 computing a third magnitude $F_P$ having terms of spacing P, the first magnitude $F_P$ being computed by the formula;
 $F_P = \text{Sum}[\text{absolute value}(D_i + D_{i+2P} - 2D_{i+P})]$, where i is an integer value of n and P is an integer not equal to either L or M;
 computing a fourth magnitude $F_Q$ having terms of spacing Q, the first magnitude $F_Q$ being computed by the formula;
 $F_Q = \text{Sum}[\text{absolute value}(D_i + D_{i+2Q} - 2D_{i+Q})]$, where i is an integer value of n and P is an integer not equal to any of L, M or P; and
 wherein the step of identifying the recording medium type further comprises comparing $F_L$, $F_M$, $F_P$, and $F_Q$.

20. The method of claim 19, wherein the step of identifying the recording medium type further comprises:
 computing a first ratio $R_1 = F_L/F_M$;
 computing a second ratio $R_2 = F_P/F_Q$; and
 determining whether $R_2 > R_1$.

* * * * *